United States Patent [19]
Nieh

[11] 4,092,316
[45] May 30, 1978

[54] SYNTHESIS OF C-ALKYL-TRIETHYLENEDIAMINES

[75] Inventor: Edward C. Y. Nieh, Austin, Tex.

[73] Assignee: Texaco Development Corporation, New York, N.Y.

[21] Appl. No.: 753,743

[22] Filed: Dec. 23, 1976

Related U.S. Application Data

[63] Continuation-in-part of Ser. No. 546,332, Feb. 3, 1975, abandoned.

[51] Int. Cl.² .............................................. C07D 24/38
[52] U.S. Cl. ..................................................... 544/351
[58] Field of Search ................................... 260/268 T

[56] References Cited

U.S. PATENT DOCUMENTS

| 3,080,371 | 3/1963 | Spielberger, et al. | 260/268 T |
| 3,112,317 | 11/1963 | Marschall, et al. | 260/268 T |
| 3,120,526 | 2/1964 | Brader | 260/268 T |
| 3,297,701 | 1/1967 | Brader, et al. | 260/268 T |
| 3,342,820 | 9/1967 | Brader | 260/268 T |

*Primary Examiner*—Jose Tovar
*Attorney, Agent, or Firm*—Carl G. Ries; Thomas H. Whaley; James L. Bailey

[57] ABSTRACT

A liquid phase synthesis of C-alkyl-triethylenediamines involves heating to elevated temperatures of from about 200° C to 300° C a suitable N-(2-hydroxyalkyl) piperazine feedstock in the presence of a catalytic amount of a pentavalent acidic phosphorus compound and then recovering the C-alkyl-triethylenediamine product from the resulting reaction product mixture.

14 Claims, No Drawings

SYNTHESIS OF C-ALKYL-TRIETHYLENEDIAMINES

This is a continuation-in-part of copending application Ser. No. 546,332, filed Feb. 3, 1975, now abandoned.

BACKGROUND OF THE INVENTION

1. Field of the Invention

This invention relates to the preparation of alkyl substituted bicycloheterocyclic compounds and more particularly pertains to a novel catalytic liquid phase process for the preparation of C-alkyl and C-polyalkyl substituted diazabicyclo-(2,2,2)-octanes, commonly referred to as C-alkyl-triethylenediamines.

2. Prior Art

Triethylenediamine is an exceptional urethane catalyst owing to the presence of two bridgehead nitrogens in the molecule. However, many times it is advantageous to substitute one or more of the ring carbons with an alkyl group in order to match solubility of constituents, increase ease of handling, reduce activity, or reduce the volatile nature of the odoriferous catalyst. C-alkyl and C-polyalkyl triethylenediamines are thus very useful as catalysts and accelerators for urethane systems.

There are several procedures known for the preparation of C-alkyl substituted diazabicyclo-(2,2,2)-octanes by catalytically cyclizing certain substituted piperazine compounds, such as N-hydroxyethyl-methylpiperazines, N,N'-dihydroxyethylmethylpiperazines, etc., in the presence of very specific types of catalysts. Generally, such known procedures are vapor phase reactions which are carried out by contacting the vapors of the substituted piperazine feedstock employed with the acidic-type catalyst at temperatures in excess of about 250° C to about 550° C. For example, U.S. Pat. No. 3,167,518 to Farkas et al discloses a method for preparing 2-methyl diazabicyclo-(2,2,2)-octane by cyclo-dehydrating the reaction product of 2-methylpiperazine with at least an equal molar quantity of ethylene oxide in vapor phase over an active silicious cracking catalyst. More particularly, it is disclosed that the vapor phase cyclodehydration reaction is carried out by passing the ethoxylated 2-methylpiperazine reaction product vapors over a silica-alumina cracking catalyst at a temperature of 325° C to 425° C.

U.S. Pat. No. 3,297,701 to Brader, Jr., et al discloses that C-substituted diazabicyclo-(2,2,2)-octanes may be synthesized by the process of contacting a substituted piperazine compound, such as N-aminoethyl-C-alkyl-piperazines, N-hydroxyethyl-C-alkyl-piperazines, etc., in vapor phase with a metal phosphate catalyst in the presence of ammonia at a reaction temperature within the range of 250° C to about 550° C. In addition, U.S. Pat. No. 3,342,820 to Brader, Jr., teaches a catalytic vapor phase process for synthesizing C-alkyltriethylenediamines employing complex phosphates as catalysts which contain in their crystalline structure an alkali metal and a trivalent element such as aluminum, boron, bismuth and iron. It is disclosed in the patent that the complex phosphate catalyst is very specific in the process for the preparation of C-alkyl-triethylenediamines. More particularly, the disclosed process is described as being carried out in vapor phase which includes passing the described substituted piperazine feedstock vapors over the complex phosphate catalyst along with ammonia at a temperature within the range of about 250° C to 550° C.

However, conventional vapor phase catalytic processes for preparing C-alkyl-triethylenediamines usually suffer from one or more of several disadvantages. For example, under the conventional vapor phase reaction conditions employed, several competing side reactions occur resulting in crude reaction product effluents which contain several undesirable by-products such as piperazine, pyrizenes, etc. Not only do such side reactions deleteriously affect the yield of the desired product, but also the by-products formed have physical properties substantially similar to the desired products. These substantially similar physical properties make it extremely difficult to separate the desired C-alkyl-triethylenediamines in pure form from the crude reaction product effluent.

U.S. Pat. No. 3,080,371 to Spielberger et al describes a liquid phase process for preparing triethylenediamine which includes heating N-hydroxyethyl piperazine or N,N'-dihydroxyethyl piperazine with a high boiling carboxylic acid catalyst in the presence of a high-boiling point solvent at temperatures between 250° and 350° C. The disclosed process employs temperatures lower than those normally employed in the above-mentioned vapor phase processes. However, the process has been found to be very slow and usually results in the formation of excessive amounts of a polymeric residue. In addition, the liquid phase process described in U.S. Pat. No. 3,080,371 is specifically directed to the preparation of triethylenediamine employing feedstocks of N-hydroxyethyl piperazine or N,N'-di-hydroxyethyl piperazine. It has been demonstrated, as described in the aforementioned U.S. Pat. No. 3,342,820 to Brader, Jr., that the catalyst requirements for making C-substituted triethylenediamines are quite different from the catalyst requirements for making triethylenediamine. Experimentation has shown that C-alkyltriethylenediamines or their precursors are more sensitive than triethylenediamine or its precursors and that unpredictably different degrees of response of initial feedstocks with different catalysts occur.

It has now been discovered that certain acidic phosphorus compounds can be used to effect a new catalytic process for preparing C-alkyl-triethylenediamines, in the liquid phase providing high selectivity and good yields of the desired product. Since the process of the instant invention is carried out in liquid phase, it does not suffer from many of the aforementioned disadvantages accompanying conventional vapor phase processes. In addition, in the invention process a novel catalyst system is employed which heretofore has not been suggested in the literature.

SUMMARY OF THE INVENTION

According to the broad aspect of the instant invention, C-alkyl-triethylenediamines are prepared from a corresponding 2-(hydroxyalkyl) piperazine feedstock by heating the feedstock in liquid phase in the presence of a catalytically effective amount of a pentavalent acidic phosphorus compound.

DETAILED DESCRIPTION OF THE PREFERRED EMBODIMENTS

In accordance with a preferred embodiment, C-alkyl substituted triethylenediamine is prepared in liquid phase by heating at elevated temperatures the corresponding N-(2-hydroxyethyl) C-alkyl substituted piperazine in the presence of a pentavalent acidic phosphorus compound. Specifically, C-methyl triethylenediamine is prepared in accordance with a preferred embodiment by initially charging a suitable reaction vessel fitted with stirring apparatus and a distillation column topped with a distillation head with N-(2-hydroxyethyl) C-methyl piperazine, a catalytic amount of phenylphosphonic acid and an inert high boiling solvent. The mixture is heated with agitation to temperatures from about 240° to 260° C. The reaction mixture is allowed to reflux with agitation for about 5 to 24 hours, during which time the C-methyl triethylenediamine product is collected overhead at head temperatures of about 150°–170° C.

The feedstocks that may be employed in accordance with the instant invention can be depicted by the formula

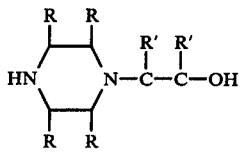

wherein each R is, independently, a hydrogen or a monovalent hydrocarbon alkyl radical of from 1 to about 6 carbon atoms and each R' is independently a hydrogen or a monovalent hydrocarbon alkyl radical of from 1 to about 4 carbon atoms providing at least one of R and R' is other than hydrogen. Preferably, each R is hydrogen or a lower alkyl radical of from 1 to about 4 carbon atoms. More preferably R and R' are, independently, hydrogen or a methyl radical. In accordance with one aspect, each R is, independently hydrogen and at least one of R' is a lower alkyl of from 1 to about 4 carbon atoms. In accordance with another aspect, each R' is independently hydrogen and at least one R is a lower alkyl of from 1 to about 4 carbon atoms.

In accordance with a preferred embodiment, at least two non-adjacent R s are lower alkyl radicals of from 1 to about 4 carbon atoms and most preferably methyl. In accordance with another preferred embodiment, at least one R and R' are lower alkyl of from 1 to about 4 carbon atoms, most preferably the hydroxy is attached to a primary carbon.

In accordance with a greatly preferred embodiment no more than two R s are methyl, and more preferably one are methyl, radicals and each R' is hydrogen.

Since, the product of the instant invention is preferably collected overhead as described hereinbefore, it is preferred that the sum of the carbon atoms of substituents R and R' number not more than about 8 and preferably about 6. Although not critical to the inventive concept, the skilled artisan should consider the number and length of substituent alkyl chain in light of known recovery processes and separation techniques.

Thus, the types of substituted piperazine feedstock which may be employed in accordance with the instant invention are generally C-lower alkyl or C-poly lower alkyl substituted piperazines containing at least one N-(2-hydroxyethyl) group and the corresponding substituted and unsubstituted piperazines containing at least one N-(2-hydroxyalkyl) group wherein the alkyl radical contains at least 3 carbon atoms. It will be realized that C-alkyl substituted piperazines containing N-(2-hydroxyalkyl) groups wherein the alkyl radical contains at least 3 carbon atoms, for example, N-(2-hydroxypropyl) or N-(2-hydroxybutyl) form C-alkyl substituted triethylenediamines in accordance with the invention by catalyzed cyclization. That is, the number 2 alkyl carbon forms a bond with the N' nitrogen of the piperazine. It will further be realized that the corresponding N,N'-(di-2-hydroxyethyl) substituted compounds can also be utilized, but one of the hydroxyethyl moieties is displaced upon cyclization.

Exemplary of piperazine feedstocks that are useful include but are not limited to N-(2-hydroxyethyl)-2-methylpiperazine, N-(2-hydroxyethyl)-3-methylpiperazine, N,N'-(di-2-hydroxyethyl)-2-methylpiperazine, N-(2-hydroxypropyl)piperazine, N,N'-(di-2-hydroxypropyl)-2,5-dimethylpiperazine and N-(2-hydroxyethyl)-2,6-dimethylpiperazine, N-(2-hydroxyethyl)-2-hexyl piperazine, N-(2-hydroxypropyl)-2-ethyl-5-methyl-6-methyl piperazine and the like. These substituted piperazine feedstocks may be employed in essentially pure form or in admixtures. These feedstocks may be conveniently prepared by known procedures such as by alkoxylating piperazine or C-alkyl and C-polyalkyl substituted piperazine with 1,2-propylene oxide or ethylene oxide in accordance with known processing techniques. For example, the hydroxyethyl- and di(hydroxyethyl)-substituted alkyl-piperazine feedstocks may be prepared by mixing and reacting a alkyl-piperazine with ethylene oxide under controlled temperature conditions. The feedstock of N-(2-hydroxypropyl)- and N,N'-(di-2-hydroxypropyl)-piperazines are prepared in substantially the same manner by employing 1,2-propylene oxide and piperazine.

The catalytic material of the instant inventive process can be broadly described as a pentavalent acidic phosphorus substance. Thus, any compound of pentavalent phosphorus which will form an acid under the reaction conditions is generally useful. Such compounds will be readily apparent to the skilled artisan. As is generally true of catalytic processes, the substrate and catalyst should be "matched" to effect the most advantageous results. Such "matching" can be readily accomplished by the skilled artisan without undue experimentation given the teachings and examples of the instant invention.

More specifically, the phosphorus acid compounds are those pentavalent phosphorus containing compounds having at least one P-O-R group wherein R is hydrogen or a univalent organic radial.

The anhydrides are the condensed acid compounds as defined above that usually contain at least one P-O-P bond.

The pentavalent acidic phosphorus compounds which are suitable include: phosphoric acid [P(O)(OH)$_3$], phosphonic acid [HP(O)(OH)$_2$], phosphenic acid [O=P(O)(OH)], phosphinic acid [H$_2$P(O)OH], along with their corresponding organo substituted acids; their corresponding acid esters; and their corresponding organo substituted acid esters.

The pentavalent phosphorus acid anhydrides or mixed anhydrides and their corresponding organo substituted compounds, including the esters and organo substituted esters are also included herein. It should be realized that, whenever corresponding acid compounds are defined hereinafter, the definition generally applies to the anhydrides as well.

The organo substituted pentavalent acidic phosphorus compounds are those generally wherein one or more of the hydrogens, attached directly to the phosphorus atom, is replaced with a monovalent organo radical, having the character of either an aliphatic or aromatic hydrocarbon. Likewise, the pentavalent acid ester compounds are those wherein one or more of the hydroxy hydrogens is replaced with a monovalent organo radical having the character of either an aliphatic or aromatic hydrocarbon. The corresponding organo substituted ester compounds are those ester compounds defined above wherein one or more of the hydrogens attached directly to the phosphorus atom is replaced with a monovalent organic radical having the character of either an aliphatic or aromatic hydrocarbon.

Preferably the acidic phosphorus compounds useful as catalysts are of the formula

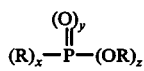

wherein R is hydrogen or a monovalent organic radical having the character of either an aliphatic or aromatic hydrocarbon; $x$ is from 0 to 2; $y$ is 1, or 2 and $z$ is from 1 to 3 and the sum of $x+y+z$ is such that P is pentavalent.

Suitable monovalent aliphatic radicals which can replace a hydrogen as described hereinabove are saturated aliphatic, acyclic and alicyclic radicals including the monocyclic and bridged alicyclic moieties. It should be realized that it is not critical that the aliphatic radical appended to the phosphorus and/or the hydroxy oxygen be completely hydrocarbon so long as the moiety attached to the phosphorus has the character of a saturated aliphatic or cycloaliphatic hydrocarbon radical. Namely, such radicals can be substituted by such as sulfur, nitrogen and analogs of the corresponding hydrocarbons, provided, of course, that the phosphorus with such appended radicals maintains the character of an acidic phosphorus moiety.

Suitable monovalent aromatic radicals which can replace a hydrogen as described hereinabove are mono- and polycyclic aromatics including the complex mono- and polycyclic arenes as well as the bridged polycyclic aromatic compounds. It should be realized that it is not critical that the aromatic radical appended to the phosphorus and/or oxygen be completely hydrocarbon so long as the moiety attached to the phosphorus or oxygen has the character of an aromatic or polycyclic aromatic hydrocarbon radical. The aromatic radical can be sutstituted with saturated aliphatic monovalent moieties as described above, provided that the phosphorus, with such appended radicals, maintains the character of an acidic phosphorus moiety.

Thus it will be realized that aryls, alkaryls, aralkyls, and like monovalent moieties can replace one or more of the hydrogens attached directly to the phosphorus atom to yield a corresponding organo substituted compound and/or replace one or more hydroxy hydrogens to yield the organo substituted ester. It will be readily apparent to those skilled in the art those compounds which are to be included within this group. Preferably the organo moieties contain from 1 to about 20 carbon atoms. More preferably, alkyl groups contain from 1 to about 12 carbon atoms, and most preferably 1 to about 8. Aryl or araryl groups preferably contain from 6 to about 20 carbon atoms and most preferably 6 to about 12. Alkaryl or aralkyl groups preferably contain 7 to about 20 carbon atoms with 6 to about 14 being preferred.

Exemplary organo substituted acid compounds include the substituted pentavalent phosphorus acid compounds. More specifically, mono phosphonic acids and the mono- and disubstituted phosphinic acids. Preferably lower alkyl substituted acids are employed wherein the alkyl group contains from 1 to 8 carbon atoms. Preferred aryl substituted acids contain from about 6 to about 20 carbon atoms and may include aryl, aralkyl, or alkaryl groups. Examples include substituted phosphonic and phosphinic acids such as diethyl phosphinic acid, diphenyl phosphinic acid, ethyl methyl phosphinic acid, phenyl phosphinic, ethyl phosphinic, ethyl phosphonic, phenyl phosphonic, naptha phosphonic, methyl phosphinic and the like.

Examples of organo acid esters include as a general class the pentavalent phosphorus acid esters. And, more specifically, the mono-, di- and tri- pentavalent acid esters which include the mono-, di- and tri organo phosphate esters, the mono- and di- organo phosphonate esters, and the monophosphinate esters. Preferably, the lower alkyl esters are employed such as those having from 1 to about 8 carbon atoms per alkyl group. Preferred aryl esters contain from about 6 to about 20 carbon atoms and may include aryl, aralkyl, or alkaryl. Examples include: dimethyl phosphate, diphenyl phosphate, triphenyl phosphate, ethyl methyl phenyl phosphate, dimethyl phenyl phosphate, ethyl phosphate, phenyl phosphate, phenyl ethyl phosphonate, phenyl phosphinate, ethyl phosphinate, isobutyl phosphonate, diphenyl methyl phosphonate, dicyclopentane napthyl phosphonate and the like.

The organo substituted pentavalent phosphorus ester compounds are also included. It will be readily apparent from the foregoing discussion the scope of these compounds. Generally, the pentavalent compounds include the mono organo substituted mono- and di- phosphonate esters, and the mono- and di-organo substituted mono phosphinate esters. Suitable such esters include: methyl-diethyl phosphinate, phenyl-diphenyl phospinate, ethyl-(triphenyl methyl) phosphonate, phenyl-phenyl phosphonate, phenyl-methyl phosphinate, diphenyl-phenyl phosphinate, methyl-ethyl phosphonate.

The above-mentioned phosphorus-containing substances are not intended to be exhaustive of those that can be employed as a catalyst in the inventive process. Those materials set forth are merely intended to be representative of the types of substances we have found to be particularly effective. Yet, of the substances and the types of compounds mentioned, we particularly prefer to employ those that are known to be most reactive such as phosphoric acid; phosphinic acids and derivatives of the formula $R_2P(O)OR'$; phosphonic acids and derivatives of the formula $RP(O)(OR')_2$ wherein each R in the above formulas is hydrogen, a lower alkyl monovalent hydrocarbon or a mono cyclic aromatic monovalent hydrocarbon radical; and wherein each R' in the above formulas is hydrogen, a lower alkyl monovalent hydrocarbon or a mono cyclic aromatic monovalent hydrocarbon radical. Most preferred are phosphoric acid; phosphinic acid; phosphonic acid; phenylphosphinic acid, ethylphosphonic acid, phenylphosphonic; methylphosphinic; methylphenyl phosphonate, dimethylphenyl phosphonate, methylphenyl phosphinate; and propylmethyl phosphonate.

The inventive process is preferably carried out by the use of a high boiling solvent that is inert under the liquid phase reaction conditions. Preferred solvents are those that have no reactive groups and have boiling points within the range of about 220° C to about 350° C. Suitable inert high boiling solvents include aromatic hydrocarbons, halogenated aromatic hydrocarbons, aromatic hydrocarbon ethers, and the like. Specific examples of a few preferred solvents include naphthalene, chlorinated benzenes, biphenyl, biphenyl ether, and diphenylmethane.

The substituted piperazine feedstock, inert high boiling solvent and acidic phosphorus compound catalyst may be admixed in any desired manner and order in carrying out the inventive process. For example, the feedstock may be initially admixed with the solvent or catalyst and then combined with the remaining solvent or catalyst, or all three admixed substantially simultaneously. The amount of solvent employed is not critical to the process of the invention. However, it is preferred to utilize about 100 to about 300 weight percent excess solvent, based upon the weight of feedstock.

Preferably, the catalyst is employed in an amount of from about 0.1 to about 20 mol percent, based upon the feedstock. The specific amount of catalyst employed has also not been found to be particularly critical and is usually determined by economics. It is particularly preferred to employ about 0.5 to about 10 mol percent catalyst.

The liquid phase reaction is then carried out by heating the substituted piperazine feedstock with the acidic phosphorus compound catalyst and solvent at a temperature within the range of about 220° C to about 300° C, preferably about 240° C to about 260° C. Although the reaction is preferably conducted at atmospheric pressure, subatmospheric or superatmospheric pressures may be employed, if desired. As the reaction proceeds under such reaction conditions, the C-alkyl-substituted triethylenediamine product thus formed and water of reaction vaporize. These vapors are preferably removed from the heated reaction zone as rapidly as possible so as to limit the formation of by-products.

Any conventional reaction equipment may be employed to carry out the liquid phase reaction. However, it is preferred to utilize a suitable reaction vessel equipped with reflux condensing means and product removal means so as to maintain the reactants within the heated reaction vessel while simultaneously removing the reaction product vapors. Moreover, the process may be carried out either batchwise, semi-continuously or continuously employing the well-known conventional techniques and apparatus for each procedure. For example, the process may be carried out semi-continuously utilizing the above-mentioned reaction vessel equipped with reflux condensing means and product removal means whereby the substituted piperazine feedstock is continuously added as the reaction product effluent is removed. The solvent, catalyst and by-product materials formed normally remain within the reaction vessel. Usually, the reaction product is taken overhead at a head temperature of about 140° C to about 210° C depending on the C-alkyl substituted product.

The C-alkyl-substituted triethylenediamine reaction product may be recovered from the crude distillate removed from the reaction zone by any of the well-known conventional techniques, such as fractional distillation, solvent extraction, and the like. One of the primary advantages of the inventive process is its high selectivity resulting in a crude distillate or reaction product mixture from which the desired product can be readily recovered without difficulty. Experiments have shown that up to 77 mol percent yield at 100% conversion may be obtained by the process of the invention. Such high selectivity substantially reduces the formation of by-products having physical properties substantially similar to the desired C-alkyl-substituted triethylenediamines.

The invention will be further illustrated by the following specific examples, which are given by way of illustration and not as limitations on the scope of this invention.

EXAMPLE I

A 500 ml 3-neck round bottom flask fitted with a mechanical stirrer, a thermometer and a thermal-jacketed distillation column topped with a distillation head was charged with 100 g. of a mixture of N-(2-hydroxyethyl)methylpiperazine (2-methyl isomer:3-methyl isomer ratio, about 1:9), 7.0 g. of phenylphosphonic acid and 150 g. of a solvent mixture of 74% biphenyl and 26% biphenyl ether, 257° C (Dow Chemical Company, Midland, Michigan, sold under the trademark DOWTHERM A). The admixture was heated to 245°–257° C for 20 hours. During this heating period, 97 g. of crude product effluent was collected overhead. The crude overhead product was then analyzed by Karl Fischer titration, and gas-liquid chromatography (GLC). The Karl Fischer titration showed 12.0% $H_2O$. The GLC analysis showed 76.0% methyl TEDA by weight. The combined analysis showed approximately a 77 mol percent yield of methyl triethylenediamine.

EXAMPLE II

Employing the same reaction equipment described in Example I, 100 g. of N-(2-hydroxyethyl)methylpiperazine (2-methyl isomer:3-methyl isomer ratio, about 1:9), 5.0 ml. of 30% aqueous phosphonic acid and 200 g. of a solvent mixture of 74% biphenyl and 26% biphenyl ether (Dow Chemical Company, Inc., Midland, Michigan, sold under the trademark DOWTHERM A) were admixed and heated to 247° C–257° C. During a period of 5 hours, 36 g. of crude reaction product was collected overhead. Analysis of the collected crude reaction product by Karl Fischer titration and GLC analysis showed it contained 11.6 g. of water and 24.4 g. methyltriethylenediamine. This yield represents about 25 mol percent methyl triethylenediamine.

EXAMPLE III

Employing the same reaction equipment described in Example 1, 100 g. of N-(2-hydroxyethyl)methylpiperazine (2-methyl isomer:3-methyl isomer ratio, about 1:9) 6.0 g. of diethyl phosphonate and 200 g. of a solvent mixture of 74% biphenyl and 26% biphenyl ether (Dow Chemical Company, Inc., Midland, Michigan, sold under the trademark DOWTHERM A) were mixed and heated to 247° C–257° C. During a period of about 6 hours, 28 g. of a crude reaction product was collected overhead. Analysis of the collected crude reaction product by Karl Fischer titration and GLC analysis showed it contained 16 g. of water and 11 g. of methyl triethylenediamine. This yield represents about 13.5 mol percent methyl triethylenediamine.

EXAMPLE IV

Employing the same reaction equipment described in Example 1, 100 g. of N-(2-hydroxypropyl)piperazine, 7 g. of phenylphosphonic acid and 150 g. of a solvent mixture of 74% biphenyl and 26% biphenyl ether (Dow Chemical Company, Inc., Midland, Michigan, sold under the trademark DOWTHERM A) were admixed and heated to 247° C–257° C. During a period of 20 hours, 25 g. of crude reaction product was collected overhead. Analysis of the collected crude reaction product by Karl Fischer titration and GLC analysis showed it contained 15 g. of water and 36 g. of methyl triethylenediamine. The yield represents about 28.5 mol percent methyl triethylenediamine.

EXAMPLE V

Employing the same reaction equipment described in Example I, 100 g (of N-(2-hydroxyethyl)methylpiperazine (2-methyl isomer:3-methyl isomer ratio, about 1:9), 7.0 g of phenylphosphinic acid and 150 g of a solvent mixture of 74% biphenyl and 26% biphenyl ether (Dow Chemical Company, Inc., Midland, Michigan, sold under the trademark DOWTHERM A) were admixed and heated to 245° C–257° C. During a period of 2.5 hours, 91 g of crude reaction product was collected overhead. Analysis of the collected crude reaction product by Karl Fischer titration and GLC analysis showed it contained 12.0 g of water and 29.5 g methyltriethylenediamine with the remainder solvent (42 g) and hydroxymethyl piperazine (6.1 g).

EXAMPLE VI

Employing the same reaction equipment described in Example I, 140 g of a mixture of N-(2-hydroxybutyl)-3-methyl piperazine and N-(2-hydroxybutyl)-2-methyl piperazine, 10 g of phenylphosphonic acid and 200 g of a solvent mixture of 74% biphenyl and 26% biphenyl ether (Dow Chemical Company, Inc., Midland, Michigan, sold under the trademark DOWTHERM A) were admixed and heated to 245° C–265° C at 500 to 400 mm Hg pressure. During a period of 14 hours, 92 g of crude reaction product was collected overhead (140° C–150° C/500 mm Hg). Analysis of the collected crude reaction product by Karl Fischer titration and GLC analysis showed it contained 12 g of water and 33 g of methylethyl triethylenediamine (isomeric mixture).

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A liquid phase process for the synthesis of C-alkyl triethylenediamines comprising the steps of:
   initially heating a piperazine feedstock selected from a group consisting of a C-lower alkyl or C-poly lower alkyl substituted piperazine containing at least one N-(2-hydroxy ethyl) group; an unsubstituted, or C-lower alkyl substituted, or C-poly lower alkyl substituted piperazine having at least one N-(2-hydroxyalkyl) group wherein the hydroxyalkyl contains at least three carbon atoms, and mixtures thereof to elevated temperatures of about 220° C to 300° C in the presence of a catalytic amount of a pentavalent acidic phosphorus compound having at least one P—O—R group wherein R is hydrogen or a univalent organic radical and, recovering said C-alkyl triethylenediamine product.

2. The process of claim 1 wherein said catalytic amount is from about 0.1 to about 20 mol percent based upon said piperazine feedstock.

3. The process of claim 1 wherein said heating is carried out in the presence of an inert high boiling solvent having a boiling point in excess of about 250° C.

4. The process of claim 1 wherein said catalyst is selected from phosphoric acid, phosphenic acid, phosphinic acid, the corresponding organo substituted acids, the corresponding acid esters, the corresponding organo substituted acid esters, and the corresponding anhydrides.

5. A liquid phase process for the synthesis of C-alkyl triethylenediamines comprising the steps of:
   initially heating a piperazine feedstock of the formula

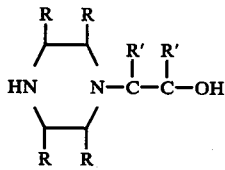

wherein each R is, independently, a hydrogen or a monovalent hydrocarbon alkyl radical of from 1 to about 6 carbon atoms and each R' is, independently, a hydrogen or a monovalent hydrocarbon alkyl radical of from 1 to about 4 carbon atoms providing at least one of R and R' is other than hydrogen, to elevated temperatures of about 220° C to 300° C in the presence of a catalytic amount of a pentavalent acidic phosphorus compound of the formula

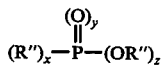

wherein R" is hydrogen or a monovalent organic radical having the character of either an aliphatic or aromatic hydrocarbon; $x$ is from 0 to 2; $y$ is 1 or 2 and $z$ is from 1 to 3 and the sum of $x+y+z$ is such that P is pentavalent; and, recovering said C-alkyl triethylenediamine product.

6. The process of claim 5 wherein said catalytic amount is from about 0.1 to about 20 mol percent based upon said piperazine feedstock.

7. The process of claim 5 wherein said heating is carried out in the presence of an inert high boiling solvent having a boiling point in excess of about 250° C.

8. The process of claim 5 wherein each R is, independently, hydrogen or a lower alkyl radical of from 1 to about 4 carbon atoms.

9. The process of claim 5 wherein each R and R' are, independently, hydrogen or a methyl radical.

10. The process of claim 5 wherein each R is, independently, hydrogen and at least one of R' is a lower alkyl of from 1 to about 4 carbon atoms.

11. The process of claim 5 wherein each R' is, independently, hydrogen and at least one R is a lower alkyl of from 1 to about 4 carbon atoms.

12. The process of claim 5 wherein at least two nonadjacent R s are lower alkyl radicals of from 1 to about 4 carbon atoms and the hydroxy is attached to a primary carbon.

13. The process of claim 5 wherein said catalyst is selected from phosphoric acid; phosphinic acids and derivatives of the formula R"$_2$P(O)OR"; phosphonic acids and derivatives of the formula R"P(O)(OR")$_2$ wherein each R" is, independently, hydrogen, a lower alkyl monovalent hydrocarbon or a mono cyclic aromatic monovalent hydrocarbon radical.

14. The process of claim 5 wherein said catalyst is selected from phosphoric acid; phosphinic acid, phosphonic acid; phenylphosphinic acid; ethylphosphonic acid; phenylphosphinic acid; methylphosphinic acid; methylphenyl phosphonate; dimethylphenyl phosphonate; methylphenyl phosphinate; and propylmethyl phosphonate.

* * * * *